(12) United States Patent
Decker et al.

(10) Patent No.: US 9,987,421 B2
(45) Date of Patent: Jun. 5, 2018

(54) INJECTABLE DRUG DELIVERY ARRANGEMENT WITH CONTROLLED DELIVERY CANNULA POSITION RELATIVE TO POINT OF DELIVERY

(71) Applicant: UNL Holdings LLC, New York, NY (US)

(72) Inventors: Robert Decker, Dillsburg, PA (US); Gautam N. Shetty, Pikesville, MD (US); Devin Sell, Drumore, PA (US)

(73) Assignee: UNL Holdings LLC, New York, NY (US)

( * ) Notice: Subject to any disclaimer, the term of this patent is extended or adjusted under 35 U.S.C. 154(b) by 38 days.

(21) Appl. No.: 14/755,589

(22) Filed: Jun. 30, 2015

(65) Prior Publication Data

US 2015/0297829 A1     Oct. 22, 2015

Related U.S. Application Data

(62) Division of application No. 13/566,626, filed on Aug. 3, 2012, now Pat. No. 9,352,084.

(Continued)

(51) Int. Cl.
*A61M 31/00*      (2006.01)
*A61M 5/158*      (2006.01)
(Continued)

(52) U.S. Cl.
CPC ............. *A61M 5/158* (2013.01); *A61F 11/00* (2013.01); *A61M 5/16813* (2013.01);
(Continued)

(58) Field of Classification Search
CPC .......... A61M 5/329; A61M 2210/0662; A61M 5/46; A61F 11/00; A61F 11/002
See application file for complete search history.

(56) References Cited

U.S. PATENT DOCUMENTS

| 6,685,697 B1 | 2/2004 | Arenberg et al. |
| 6,740,059 B2 | 5/2004 | Flaherty |

(Continued)

FOREIGN PATENT DOCUMENTS

| EP | 2 016 963 A1 | 1/2009 |
| JP | 2004-521667 | 6/2004 |

(Continued)

OTHER PUBLICATIONS

European Patent Office, International Search Report in International Patent Application No. PCT/US2012/049575 (dated Oct. 31, 2012).

(Continued)

*Primary Examiner* — Emily Schmidt
(74) *Attorney, Agent, or Firm* — Hamilton, Brook, Smith & Reynolds, P.C.

(57) ABSTRACT

A cannula for administration of a medicine to a target location includes a tube with at least one nodule disposed along the circumferential surface and spaced at a defined distance from the distal end of the tube. An arrangement for delivery of a medicine to a target location includes the cannula and a pump fluidly coupled to the cannula. The distal end of the cannula may be inserted into a target location until the nodule reaches a surface that limits a depth of penetration before delivery of the medication.

17 Claims, 3 Drawing Sheets

Related U.S. Application Data

(60) Provisional application No. 61/515,547, filed on Aug. 5, 2011.

(51) Int. Cl.
*A61F 11/00* (2006.01)
*A61M 5/32* (2006.01)
*A61M 5/46* (2006.01)
*A61M 5/168* (2006.01)

(52) U.S. Cl.
CPC .............. *A61M 5/329* (2013.01); *A61M 5/46* (2013.01); *A61M 2005/1585* (2013.01); *A61M 2005/1587* (2013.01); *A61M 2210/0668* (2013.01); *Y10T 29/49826* (2015.01)

(56) References Cited

U.S. PATENT DOCUMENTS

| | | | |
|---|---|---|---|
| 7,206,639 B2 | 4/2007 | Jacobsen et al. | |
| 7,387,614 B2 | 6/2008 | Staecker | |
| 8,337,471 B2 | 12/2012 | Baid | |
| 2002/0082554 A1* | 6/2002 | Lenarz | A61F 11/00 604/104 |
| 2002/0169416 A1* | 11/2002 | Gonnelli | A61M 5/14248 604/142 |
| 2004/0172005 A1 | 9/2004 | Arenberg et al. | |
| 2005/0131345 A1 | 6/2005 | Miller | |
| 2006/0264897 A1 | 11/2006 | Lobl et al. | |
| 2007/0060837 A1 | 3/2007 | Cho et al. | |
| 2008/0065002 A1 | 3/2008 | Lobl et al. | |
| 2008/0071246 A1 | 3/2008 | Nazzaro et al. | |
| 2008/0132824 A1* | 6/2008 | Epley | A61F 11/00 604/21 |
| 2009/0124973 A1 | 5/2009 | D'Agostino et al. | |
| 2010/0106134 A1 | 4/2010 | Jolly et al. | |
| 2011/0112508 A1 | 5/2011 | Panzirer | |
| 2011/0208161 A1 | 8/2011 | Ivri | |

FOREIGN PATENT DOCUMENTS

| | | |
|---|---|---|
| JP | 2010-533533 | 10/2010 |
| JP | 2011-010999 | 1/2011 |
| WO | WO 2002/020073 | 3/2002 |
| WO | WO 2009/010847 | 1/2009 |
| WO | WO 2010-100241 A1 | 9/2010 |

OTHER PUBLICATIONS

European Patent Office, Written Opinion of the International Searching Authorty in Interntional Patent Application No. PCT/US2012/049575 (dated Oct. 31, 2012).

* cited by examiner

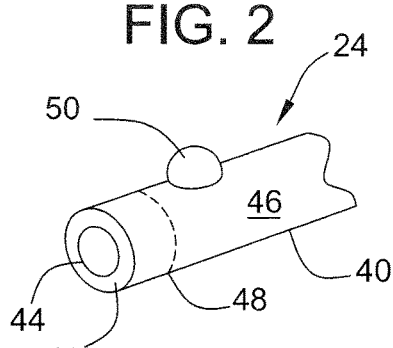
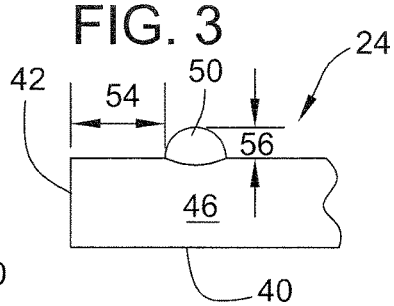
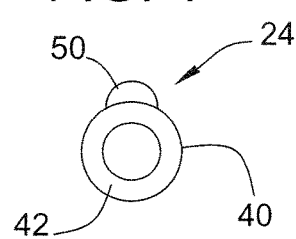
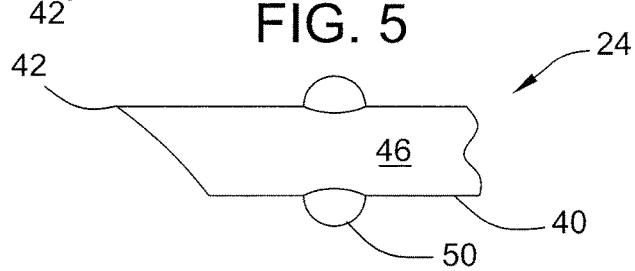
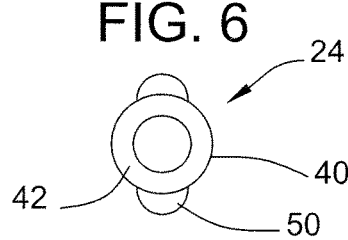
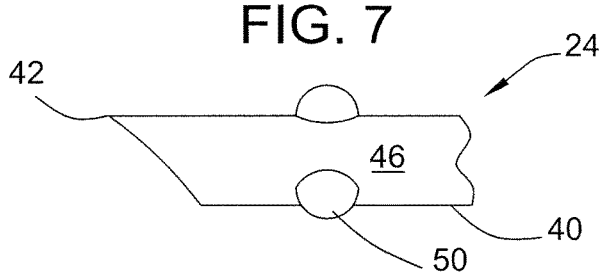
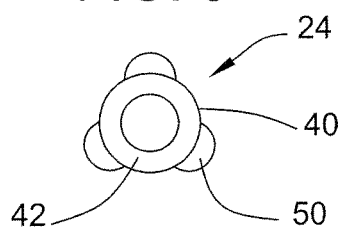
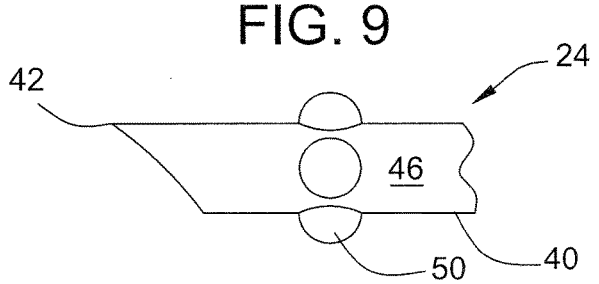
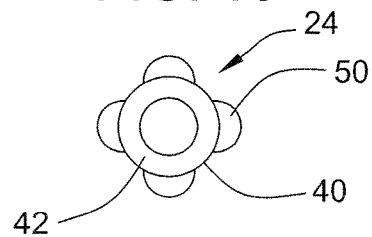
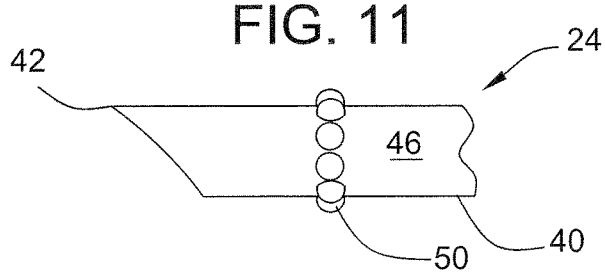
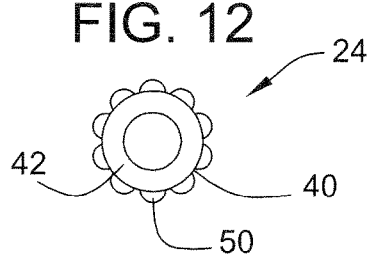

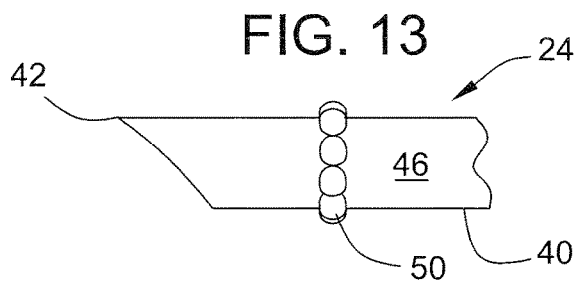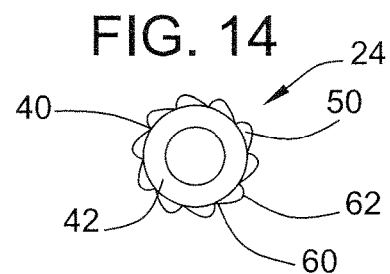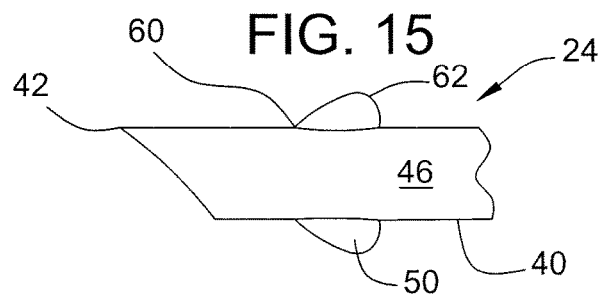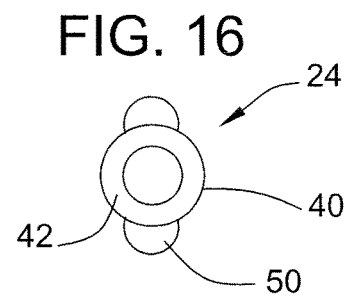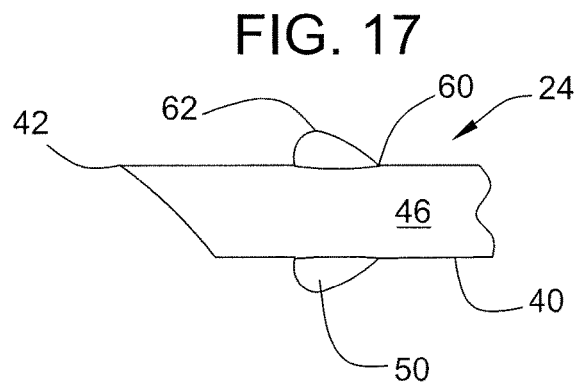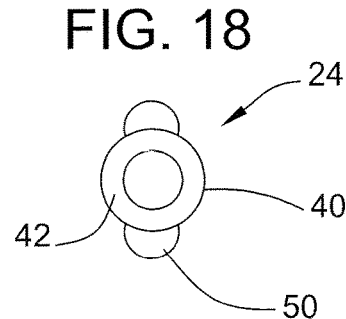

INJECTABLE DRUG DELIVERY ARRANGEMENT WITH CONTROLLED DELIVERY CANNULA POSITION RELATIVE TO POINT OF DELIVERY

CROSS-REFERENCE TO RELATED APPLICATIONS

This application is a divisional of U.S. application Ser. No. 13/566,626 filed Aug. 3, 2012, which claims priority to U.S. Provisional Patent Application 61/515,547, which was filed on Aug. 5, 2011, both of which are included herein by reference in their entirety for all purposes.

TECHNICAL FIELD

This patent disclosure relates generally to systems for the delivery of medicine, and, more particularly to structures for controlling the depth of penetration of a delivery cannula relative to a point of delivery.

BACKGROUND

The delivery of medications by injection may be in the form of a single administration(s), or a series of administrations that occur at predetermined intervals over a set time period. Medication can be delivered using a pump to a cannula that is placed into the target bone or tissue. Pumps for delivering the medication may be, for example, in the form of a syringe or a primary drug container, that is actuated to deliver a predetermined volume of medicine at set times or time intervals, or in response to a delivery trigger.

A number of injectable medication delivery applications require the placement of the delivery cannula remotely from the pump. In such applications, the delivery cannula may be fluidly coupled to the pump by flexible tubing, which allows for required placement of the cannula, convenient placement of the pump, and provides flexibility to the clinician to manipulating the medication delivery setup. For example, the pump may be supported on the surface of a table or in a bag, or on the patient's body itself.

Accurate placement of the cannula requires not only accurate placement for insertion, but also precise depth insertion. In this regard, it is desirable that there be minimum interference with the line of sight to the patient end of the cannula so the medical personnel may clearly visualize the penetrating end of the cannula along with the target tissue or bone. Ensuring delivery of medication at the correct depth is critical to maximizing efficacy of many medications and compliance with indicated route of administration. For example, too deep of penetration of a cannula may result in intramuscular delivery as opposed to an intended subcutaneous delivery, while too shallow penetration may result in subcutaneous delivery, as opposed to an intended intramuscular delivery.

SUMMARY

The disclosure describes, in one aspect, a cannula for use in the administration of a medicine to a target location. The cannula includes a tube having a proximal end and a distal end, a lumen extending between the proximal and distal ends, and an outer circumferential surface defining a circumference. At least one nodule is disposed along the outer circumferential surface and spaced at a defined distance from the distal end of the tube. The at least one nodule may be utilized as depth limiters to control the depth of cannula insertion at a target location.

In one embodiment, the cannula may be utilized for administration of a medicine to a targeted location into the inner ear. The cannula may be inserted through an ear canal of an ear such that the distal end of the cannula and the at least one nodule are caused to pass through a tympanic membrane. The distal end of the cannula may be placed adjacent to or in contact with a target location at the membrane wall of the inner ear such that the at least one nodules limit the insertion depth of the cannula into the wall. The medicine may then be administered to the target location. The at least one nodule may be sized, shaped, arranged and/or otherwise configured to permit passage through one or more membranes, such as the tympanic membrane, while not permitting passage through other membranes, such as the temporal bone lining the inner ear.

The disclosure describes, in another aspect, an arrangement for delivery of a medicine to a target location. The arrangement includes a cannula and a pump fluidly coupled to the cannula. The cannula includes a tube having a proximal end and a distal end, a lumen extending between the proximal and distal ends, and an outer circumferential surface defining a circumference. The at least one nodule is disposed along the circumferential surface and spaced at a defined distance from the distal end of the tube.

The disclosure describes, in yet another aspect, a method of delivering a medicine to a target location. The method includes the steps of positioning the distal end of a cannula for insertion into the target location, inserting the distal end of the cannula into the target location until a nodule disposed on the outer surface of the cannula reaches a surface that limits a depth of penetration into the target location, and delivering the medicine through the cannula to the target location.

The disclosure describes, in a further aspect, a method of fabricating the cannula comprising the steps of providing a tube, and forming the at least one nodule on the outer surface of the tube by at least one of metal stamping, precision welding, injection molding, needle overmold, adhesion, interference fit, and electrochemical deposition, and combinations thereof.

BRIEF DESCRIPTION OF THE DRAWING(S)

FIG. 2 is an enlarged fragmentary isometric view of an end of a cannula of FIG. 1 according to aspects of the disclosure.

FIG. 3 is an enlarged fragmentary side elevational view of the end of the cannula of FIG. 2.

FIG. 4 is an end view of the cannula of FIG. 2.

FIG. 5 is an enlarged fragmentary side elevational view of an end of another embodiment of a cannula according to aspects of the disclosure.

FIG. 6 is an end view of the cannula of FIG. 5.

FIG. 7 is an enlarged fragmentary side elevational view of an end of another embodiment of a cannula according to aspects of the disclosure.

FIG. 8 is an end view of the cannula of FIG. 7.

FIG. 9 is an enlarged fragmentary side elevational view of an end of another embodiment of a cannula according to aspects of the disclosure.

FIG. 10 is an end view of the cannula of FIG. 9.

FIG. 11 is an enlarged fragmentary side elevational view of an end of another embodiment of a cannula according to aspects of the disclosure.

FIG. 12 is an end view of the cannula of FIG. 11.

FIG. 13 is an enlarged end view of another embodiment of a cannula according to aspects of the disclosure.

FIG. 14 is an end view of the cannula of FIG. 13.

FIG. 15 is an enlarged fragmentary side elevational view of an end of another embodiment of a cannula according to aspects of the disclosure.

FIG. 16 is an end view of the cannula of FIG. 15.

FIG. 17 is an enlarged fragmentary side elevational view of an end of another embodiment of a cannula according to aspects of the disclosure.

FIG. 18 is an end view of the cannula of FIG. 17.

DETAILED DESCRIPTION

Figure 1:
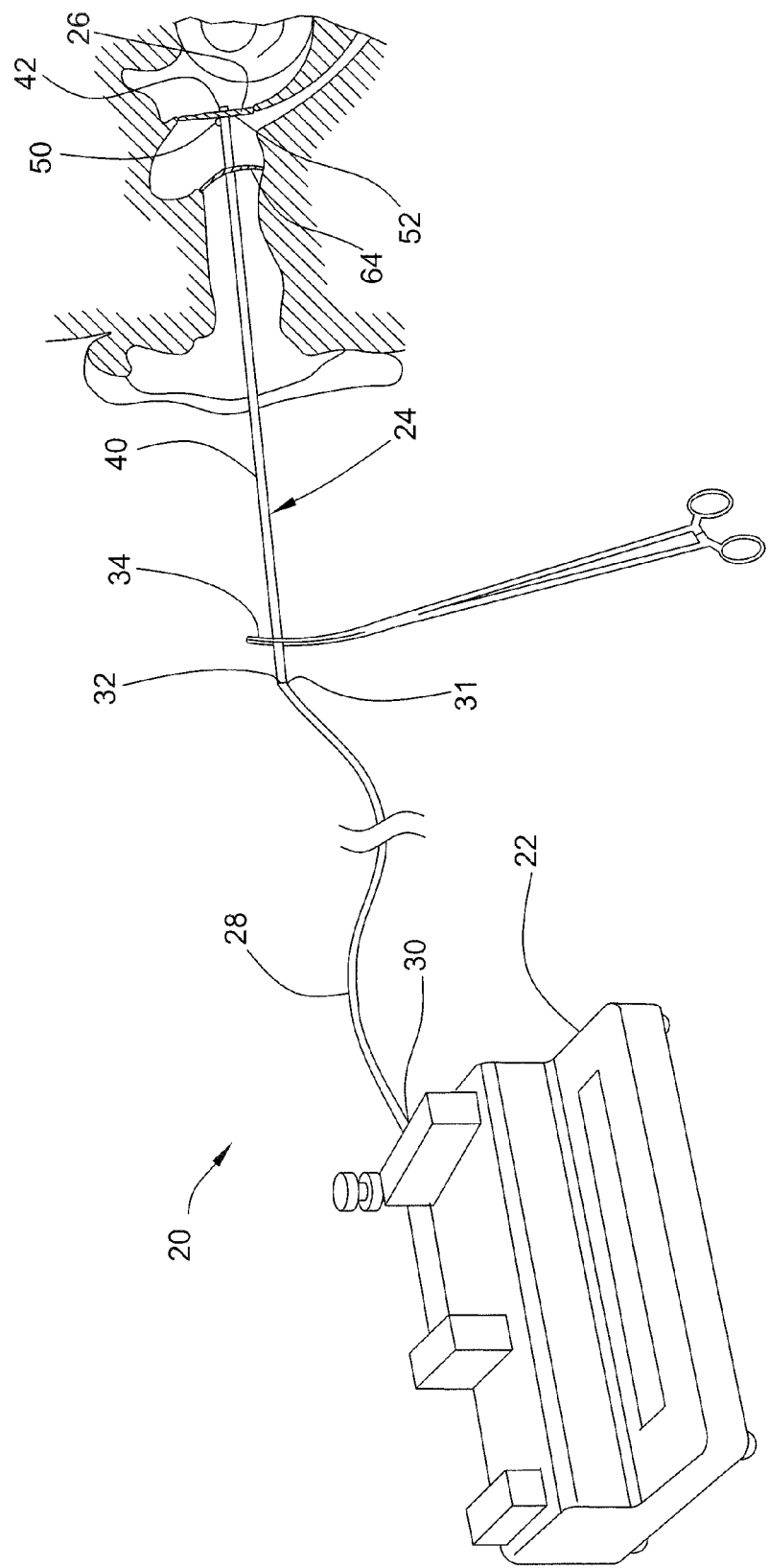
FIG. 1 is a schematic view of a medicine delivery system according to aspects the disclosure.

The invention relates to a device and method for controlling the position of a medicine delivery cannula, and related methods of manufacturing and methods of use. Accurate positioning of a delivery cannula and dispensing of medication to a target location is critical to the efficacy, compliance, and success of many medical treatments. The present invention provides a device and methodology for targeting the delivery cannula and the appropriate depth in a target membrane to improve the administration of such treatments. Utilizing the present inventions for drug delivery to targeted location may greatly improve the efficacy of the treatment, ease or simplify the surgical operation of the physician, and decrease the amount of pain or discomfort felt by the patient. For example, certain treatments must be delivered to the inner ear. Too shallow penetration of a cannula in this sensitive location may result in inaccurate or incomplete delivery of the medication while too deep penetration may cause substantial pain and/or harm to the patient. The embodiments of the present invention function to ensure that the accurate depth for drug delivery is reached, thereby maximizing drug efficacy while maintaining or improving patient comfort.

Turning to FIG. 1, there is illustrated an arrangement 20 for administration of a medicine. For purposes of this disclosure, the term "medicine" is intended to include a substance or preparation used in treating disease or a health condition, maintaining health, or treating, preventing, alleviating, or curing of disease or a health condition. The term "medicine" may include, for example, gaseous, liquid, and powder form pharmaceutical treatments. The device may be used in a number of locations for drug delivery such as, for example, the inner ear of a patient, as illustrated in FIG. 1.

The arrangement 20 includes a pump 22 that is fluidly connected to a cannula 24 for administration of the medicine to a target location 26, such as within a tissue or within a bone. The pump 22 may include any appropriate administration device, such as, by way of example only, a syringe, or some other container the holds the medicine for delivery, and may be manually or automatically actuated. The pump 22 provides one or more of a single administration of medicine, administration of medicine over period of time, administration of medicine at controlled intervals, or administration of medication upon manual activation.

The pump 22 may be fluidly coupled directly to the cannula 24, or, as shown in FIG. 1, the pump 22 may be fluidly coupled to the cannula 24 by a secondary cannula or tubing 28, which serves as a medicine pathway to the delivery cannula 24. The tubing 28 may be of any appropriate design and material. By way of example, the tubing 28 may be formed of polyurethane tubing or another suitable material. The proximal end 30 of the tubing 28 is securely coupled to the pump 22, while the distal end 31 of the tubing 28 is coupled to a proximal end 32 of the cannula 24 by any appropriate method, such as an interference fit or partial, controlled dissolution of the material of the tubing 28. A control clamp 34, such as the illustrated hemostat, may be provided to further control flow of medicine through the arrangement and may, optionally, be used to control flow. It will be appreciated that the flexibility and length of the tubing 28 allow the pump 22 to be disposed at a location that is a distance from the cannula 24. In this way, the pump 22 may be disposed on a support surface, such as a table (not illustrated), carried in a pouch or pocket (not illustrated), or disposed directly on or in body tissue (not illustrated). Alternatively, as stated above, a syringe or other primary drug container may be utilized to initially store the treatment and dispense it for delivery to the targeted location.

The delivery cannula 24 includes a tube 40 with a proximal end 32, where a drug treatment may be introduced, and a distal end 42, where a drug treatment may be dispensed, and a lumen 44 (see FIG. 2) extending between the proximal and distal ends 32, 42 along a longitudinal axis. The distal end 42 may be blunt, as illustrated in FIGS. 1-4, or beveled to a sharp tip, as illustrated in FIGS. 5-18, for example. The outer surface 46 of the cannula 24 is generally circumferential, and defines a circumference 48. In use, the distal end 42 of the cannula 24 is inserted into the target location 26 such that medicine from the pump 22 may be delivered through the tubing 28 (if included) and the lumen 44 of the cannula 24 to the target location 26.

The cannula 24 may be made of a number of materials, such as, for example, plastic or metal. The cannula 24 may be a rigid cannula or a soft cannula. In at least one embodiment, the cannula 24 is a rigid steel cannula with no bevel.

According to a feature of this disclosure, the cannula 24 includes an injection depth regulating arrangement in the form of at least one nodule 50 that is disposed along the circumferential outer surface 46 and spaced from the distal end 42 of the tube 40. When the distal end 42 of the cannula 24 is inserted into the target location 26, the nodule 50 will contact a surface 52 to control the penetration depth of the cannula 24. It will be appreciated that surface 52 may be a surface of the target location 26 for medicine delivery, or the surface 52 may be an alternate surface. By way of example only, if the target location 26 is bone, the surface 52 may be the surface of a tissue covering the bone. Thus, the nodule 50 provides a positive stop for the clinician/end user/patient to press against the surface 52 for administration of the medicine, with the distance 54 of the nodule 50 from the distal end 42 of the cannula 24 and the at least one nodule 50 functioning to limit the penetration into the target location 26.

The one or more nodules 50 may be located on the outer surface of the cannula 24 at any desirable location along its longitudinal axis. For example, the one or more nodules 50 may be located at or near the distal end 42 of the cannula 50 in one or more embodiments, while one or more nodules 50 may be located at or near the proximal end 32 of the cannula 50 in one or more alternate embodiments. By way of example only, in various embodiments, the distance 54 of the nodule 50 from the distal end 42 of the cannula 24 may be on the order of 0.1 mm, 0.2 mm, or 0.5 mm in a blunt tipped cannula 24, or any other appropriate distance. It will be appreciated that the distance 54 may be adjusted in a cannula 24 having a sharpened tip.

The cannula 24 may include one nodule 50, or a plurality of nodules 50. The cannula 24 may include two nodules 50 as shown, for example in FIGS. 5-6, or three nodules 50 as shown, for example in FIGS. 7-8, or four nodules 50 as shown, for example in FIG. 9-10, or any number of nodules 50. It will be appreciated that the nodules 50 may be substantially evenly spaced about the circumference, as shown in FIGS. 5-10, or they may be unevenly spaced (not shown). Alternately, the nodules 50 may be disposed substantially adjacent one another about the circumference, as shown, for example, in FIGS. 11-12. Furthermore, the nodules may be disposed substantially adjacent one another about the circumference such that they effectively form an outer ring. Moreover, the nodules 50 may be disposed about the circumference in a plane disposed at a right angle to the axis of the cannula 24, as illustrated, or, for example, in a plane disposed at an angle to the axis of the cannula 24 (not shown). Nodules 50 disposed in an angled plane may be particularly useful, for example, when the cannula 24 is to rest against the target location 26 at an angle. Angular positioning of the distal end 42 of the cannula 24 at a target location 26 may alternatively be achieved by positioning one or more nodules distal or proximal to the location of one or more other nodules, such that they are located at different distances from the same reference point on the cannula. When two or more of these unevenly spaced nodules come in contact with the target location, they cannula 24 will be caused to rest at an angle to the target location.

The height 56 and outer shape of the nodules 50 may have the same or different cross-sectional profiles in embodiments of the cannula 24. The nodules 50 illustrated in FIGS. 1-12 are substantially hemispherically shaped, although they may be alternately shaped. For example, the nodules 50 may have the shape of a cone, triangle, pyramid, or a sphere having a segment removed, or the shape of a segment of a sphere, or the shape of an ellipse. The nodules 50 may be oval, square, rectangular, or trapezoidal. Those of skill in the art will appreciate, however, that smooth structures may minimize opportunities for the nodules 50 to catch on tissue as the distal end 42 of the cannula 24 is moved toward or away from the target location 26, and may minimize opportunities for any possible damage to such tissue or the target location 26.

By way of further example, the nodules 50 may have a ramped shape, that is, they may include a base end 60 that increases to a peak end 62 at which the nodule 50 displays the greatest height 56, as shown, for example, in FIGS. 13-18. In this regard, the nodules 50 may be disposed with the base end 60 of one nodule 50 substantially adjacent the peak end 62 of another nodule 51, as shown, for example, in FIGS. 13-14. Alternately, ramp-shaped nodules 50 may be disposed substantially parallel to the axis of the cannula 50, as shown in FIGS. 15-18. It will be appreciated that such a ramped structure may facilitate insertion of the cannula 50 during placement or retraction of the cannula 50 during removal of the cannula 50 following the administration of medicine. For example, a cannula 24 having the ramp-shaped nodules 50 placed as illustrated in FIGS. 15 and 16 may facilitate movement of the distal end 42 of the cannula 24 completely through a tissue before reaching a target location 26, or removal following administration if the ramp-shaped nodules 50 are placed as illustrated in FIGS. 17 and 18. For example, in the administration location as illustrated in FIG. 1, the distal end 42 of the cannula 24 may be moved through the tympanic membrane 64 before reaching the ultimate target location 26. The utilization of ramp-shaped nodules 50 may assist in this placement or removal.

It will be appreciated by those of skill in the art that the extent to which the cannula 24 penetrates into the target location 26 is determined by distance 54 of the nodule 50 from the distal end 42 of the cannula 24, the height 56 of the nodule 50 (measured perpendicularly to the axis of the cannula 24), and the shape of the nodule 50, as well as the compressibility of the target location 26. Thus, the design of the cannula 24 may be tailored to the application and target location 26 for which it will be utilized.

The cannula 24 may be fabricated by any appropriate method. The nodules 50 may be pre-formed as part of the cannula 24 or may be added to the cannula 24 by a number of manufacturing methodologies. For example, the one or more nodules 50 may be welded, such as by micro-welding, to the tube 40. In such configurations, the material of the welded nodules 50 may be a similar/identical material from that of the cannula 24. In at least one embodiment, the one or more nodules 50 are steel nodules welded to a rigid steel tube 40. Alternatively, the nodules 50 may be mounted, attached, formed, or otherwise fixed to the tube 40 by methods known in the art including metal stamping, precision welding, injection molding, needle overmold, adhesion, interference fit, and electrochemical deposition, among others. Some fabrication methods, for example, precision welding, may be done in the absence of oxygen or in an inert atmosphere to prevent oxidation of the cannula 24. The choice of fabrication method may be contingent on application and the material of the cannula 24 and of the nodules 50.

According to one method, multiple nodules 50 are laser welded to the outer surface 46 of the tube 40 in an atmosphere of inert gas. The laser is utilized to smooth the intersection of the nodules 50 at the outer surface 46 after forming each nodule 50 or on completion of all nodules. The cannula 24 may then be abrasive bead blasted or deburred by any appropriate method. Preferably, each cannula 24 is inspected to ensure both weld strength and integrity of the lumen 44.

In summary, the cannula 24 containing the one or more depth limiting nodules 50 may be used in a number of different applications. Generally, the cannula 24 may be used to deliver drug treatments to a target location 26 at a particular depth. For example, the cannula 24 may be utilized for drug delivery into bone, such as the temporal bone for inner ear delivery of drug. Similarly, the cannula 24 may be utilized for intramuscular delivery, intradermal delivery, subcutaneous delivery, or any other indicated route of administration, where the delivery is to be targeted at a particular depth. Inasmuch as the cannula 24 includes discrete nodules 50, the nodules 50 do not obstruct or only minimally obstruct the distal end 42 of cannula 24 during placement, providing medical personnel with a line of sight and hence enhanced opportunity for accurate placement.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of delivering a medicine to a target location, the method comprising:
   positioning a distal end of a cannula for insertion into a first tissue, the cannula including a steel tube defining a proximal end and the distal end of the cannula and a nodule welded along an outer circumferential surface of the steel tube and spaced at a defined distance from the distal end, the steel tube having a constant circular cross-section defining a circumference and a lumen extending between the proximal and distal ends, said nodule extending less than about the entire circumference of the tube,
   inserting the distal end of the cannula into the first tissue,
   advancing a portion of the tube through the first tissue,
   penetrating the nodule through the first tissue while advancing the tube through the first tissue,
   continuing to advance the tube through the first tissue to position the distal end of the cannula for insertion into the target location,
   inserting the distal end of the cannula into the target location, a depth of insertion into the target location limited by the nodule, and
   delivering the medicine to the target location through the lumen.

2. The method of claim 1 wherein inserting the distal end of the cannula into the target location includes advancing the distal end into the target location until the nodule is disposed adjacent the target location.

3. The method of claim 1 further including removing the distal end of the cannula from the target location and the first tissue.

4. The method of claim 1 wherein inserting the distal end of the cannula into the first tissue, advancing the portion of the tube through the first tissue, penetrating the nodule through the first tissue while advancing the tube through the first tissue, continuing to advance the tube through the first tissue to position the distal end of the cannula for insertion into the target location, and inserting the distal end of the cannula into the target location include movement of the tube in an axial direction of the cannula relative to at least one of the first tissue and the target location.

5. The method of claim 1 wherein inserting the distal end of the cannula into the target location includes inserting the distal end of the cannula into at least one of a tissue or bone.

6. The method of claim 1 wherein the delivering the medicine includes pumping the medicine from a pump.

7. The method of claim 6 wherein pumping the medicine includes manually activating the pump to deliver the medicine.

8. The method of claim 6 further including fluidly coupling at least one of a secondary cannula and tubing between the cannula and the pump.

9. The method of claim 1 further including controlling flow through the lumen with a control clamp.

10. The method of claim 1 wherein the delivering the medicine includes fluidly coupling a syringe and the cannula, and operating the syringe to deliver medicine through the lumen.

11. The method of claim 1 wherein positioning the distal end of the cannula for insertion into the first tissue includes advancing the distal end through an ear canal for insertion into a tympanic membrane, inserting the distal end of the cannula into the first tissue includes inserting the distal end into the tympanic membrane, advancing the portion of the tube through the first tissue includes advancing the portion through the tympanic membrane, and penetrating the nodule through the first tissue while advancing the tube through the first tissue includes penetrating the nodule through the tympanic membrane while advancing the tube through the tympanic membrane.

12. The method of claim 11 wherein continuing to advance the tube through the first tissue to position the distal end of the cannula for insertion into the target location includes continuing to advance the tube through the tympanic membrane to position the distal end of the cannula for insertion into an inner ear target location, inserting the distal end of the cannula into the target location includes inserting the distal end of the cannula into the inner ear target location, and delivering the medicine to the target location through the lumen includes delivering the medicine to the inner ear target location through the lumen.

13. The method of claim 12 wherein the inner ear target location includes at least one of a membrane, a bone, and a temporal bone lining the inner ear.

14. A method of delivering a medicine to an inner ear, the method comprising:
   advancing a distal end of a cannula through an ear canal, the cannula including a tube defining a proximal end and the distal end of the cannula and a nodule along an outer circumferential surface of the tube and spaced at a defined distance from the distal end, the tube having a lumen extending between the proximal and distal ends, said nodule extending less than about an entire circumference of the tube,
   positioning the distal end of the cannula for insertion into a tympanic membrane,
   inserting the distal end of the cannula into the tympanic membrane,
   advancing a portion of the tube through the tympanic membrane,
   penetrating the nodule through the tympanic membrane while advancing the tube through the tympanic membrane,
   continuing to advance the tube through the tympanic membrane to position the distal end of the cannula for insertion into an inner ear target location,
   inserting the distal end of the cannula into the inner ear target location,
   advancing the distal end into the inner ear target location until the nodule limits a depth of penetration into the inner ear target location, and
   delivering the medicine to the inner ear target location through the lumen.

15. The method of claim 14 wherein the nodule abuts the inner ear target location to limit the depth of penetration.

16. The method of claim 14 wherein the inner ear target location includes at least one of a membrane, a bone, and a temporal bone lining the inner ear.

17. The method of claim 14 wherein the delivering the medicine includes pumping the medicine from a pump.

\* \* \* \* \*